United States Patent
Montalbano et al.

(10) Patent No.: US 10,052,581 B1
(45) Date of Patent: Aug. 21, 2018

(54) PROCESS FOR RECOVERY OF CRACKER FEED FROM DRY GAS

(71) Applicant: UOP LLC, Des Plaines, IL (US)

(72) Inventors: Joseph A. Montalbano, Elmhurst, IL (US); W. Jay Lechnick, Glen Ellyn, IL (US); Xin X. Zhu, Long Grove, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/710,529

(22) Filed: Sep. 20, 2017

(51) Int. Cl.
| | |
|---|---|
| *C07C 5/08* | (2006.01) |
| *C07C 5/09* | (2006.01) |
| *B01D 53/22* | (2006.01) |
| *C01B 3/52* | (2006.01) |
| *C07C 7/144* | (2006.01) |
| *C07C 9/04* | (2006.01) |

(52) U.S. Cl.
CPC .............. *B01D 53/225* (2013.01); *C01B 3/52* (2013.01); *C07C 7/144* (2013.01); *C07C 9/04* (2013.01); *C01B 2203/0233* (2013.01); *C01B 2203/0827* (2013.01)

(58) Field of Classification Search
CPC .................................. C07C 5/08; C07C 5/09
USPC ......................................... 585/259, 264, 809
See application file for complete search history.

(56) References Cited

U.S. PATENT DOCUMENTS

| | | |
|---|---|---|
| 4,720,293 A | 1/1988 | Rowles et al. |
| 6,444,869 B2 | 9/2002 | Senetar et al. |
| 7,041,271 B2 | 5/2006 | Drnevich et al. |
| 7,763,165 B1 | 7/2010 | Schultz |
| 2009/0112028 A1* | 4/2009 | Schultz ................ C07C 2/66 585/314 |
| 2012/0053383 A1 | 3/2012 | Malaty et al. |

OTHER PUBLICATIONS

Luo, "Modelling and process analysis of hybrid hydration—absorption column for ethylene recovery from refinery dry gas", Fuel 158 (2015) 424-434.

* cited by examiner

*Primary Examiner* — Thuan D Dang

(57) ABSTRACT

A process for recovering a steam cracking feed from FCC absorber off-gas comprising ethylene, ethane and heavier hydrocarbons and light gases involves removing hydrogen, nitrogen, sulfur species, carbon monoxide/dioxide, methane and other impurities from the off-gas. An absorption zone is upstream of an acetylene selective hydrotreating reactor to remove sufficient hydrogen sulfide that can poison the selective hydrotreating catalyst but leave sufficient sulfur in the feed stream to prevent temperature runaway.

20 Claims, 1 Drawing Sheet

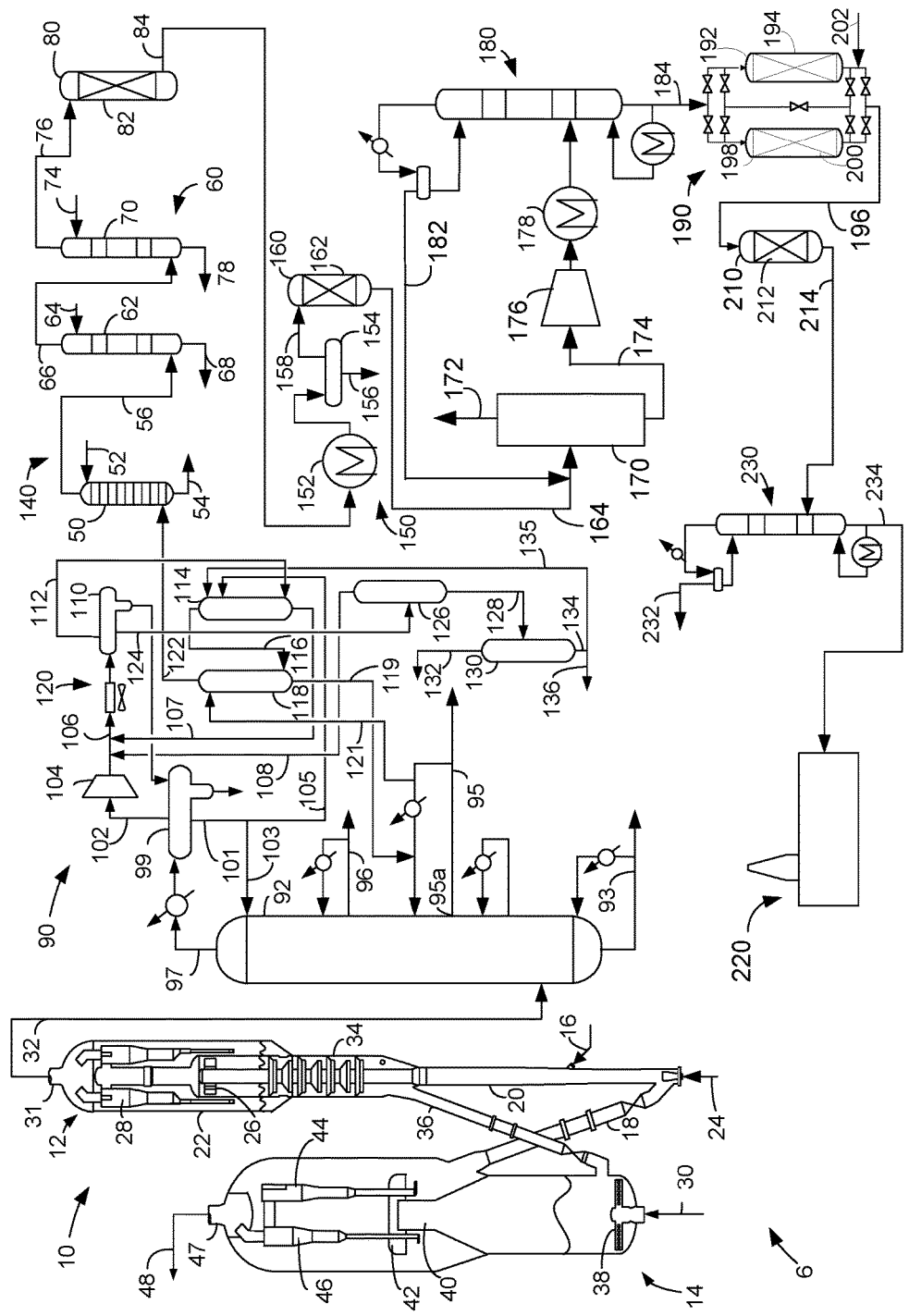

PROCESS FOR RECOVERY OF CRACKER FEED FROM DRY GAS

FIELD

The field relates to processes and apparatuses for recovery of steam cracker feed. More particularly, the technical field relates to processes and apparatuses for recovery of steam cracker feed from FCC absorber off-gas.

BACKGROUND

In a typical Fluid Catalytic Cracking (FCC) unit, the absorber off-gas, also known as dry gas, contributes to approximately one-third of the refinery fuel gas production. Dry gas is the common name for the absorber off-gas stream that contains all the gases with boiling points lower than ethane. The remaining stream is known as the FCC dry gas. A typical dry gas stream contains 5 to 50 wt % ethylene, 10 to 20 wt % ethane, 5 to 20 wt % hydrogen, 5 to 20 wt % nitrogen, about 0.05 to about 5.0 wt % of carbon monoxide and about 0.1 to about 5.0 wt % of carbon dioxide and less than 0.01 wt % hydrogen sulfide and ammonia with the balance being methane and other impurities.

The ethylene and heavier hydrocarbons in the dry gas are valuable components. Ethane can be good feed source for an ethane cracking facility for ethylene production and ethylene can be recovered for polyethylene production. Currently most ethylene and ethane in the dry gas is burned instead of recovered because the off-gas contains so many contaminants that are uneconomical to remove. However, dry gas streams still contain attractive quantities of ethylene, ethane and heavier components if recovery could be made economical.

An FCC unit that processes 7,949 kiloliters (50,000 barrels) per day will generate and burn as much as 181,000 kg (200 tons) of dry gas containing about 36,000 kg (40 tons) of ethylene and 14,400 kg (16 tons) of ethane as fuel per day. Because a large price differential exists between fuel gas and pure ethylene or steam cracker feed it would be economically advantageous to recover this ethylene and ethane from dry gas. However, the dry gas stream contains dilute impurities that can poison catalyst or impair ethylene recovery, but their removal is not economically justified by gas recovery systems. Impurities in dry gas include: hydrogen sulfide, mercaptans, carbonyl sulfide, carbon dioxide, carbon monoxide, nitrogen, nitrous oxides, oxygen, acetylene, ammonia, chlorides, and arsenic.

Accordingly, it is desirable to provide apparatuses and processes for the removal of impurities from dry gas to allow recovery and use of ethylene and ethane in a safe and a cost-effective manner.

BRIEF SUMMARY

A process for recovering a steam cracking feed from FCC absorber off-gas comprising ethylene, ethane and heavier hydrocarbons and light gases involves removing hydrogen, nitrogen and methane and other impurities from the off-gas. An absorption zone is upstream of an acetylene selective hydrotreating reactor to remove sufficient hydrogen sulfide that can poison the selective hydrotreating catalyst but leave sufficient sulfur in the feed stream to prevent temperature runaway.

BRIEF DESCRIPTION OF THE DRAWING

The FIGURE is a schematic diagram of a process and an apparatus for recovery of a steam cracker feed in accordance with an exemplary embodiment.

Definitions

As used herein, the term "stream" can include various hydrocarbon molecules and other substances.

The notation "$C_x$" means hydrocarbon molecules that have "x" number of carbon atoms, $C_x^+$ means hydrocarbon molecules that have "x" and/or more than "x" number of carbon atoms, and $C_x^-$ means hydrocarbon molecules that have "x" and/or less than "x" number of carbon atoms.

As used herein, the term "zone" can refer to an area including one or more equipment items and/or one or more sub-zones. Equipment items can include one or more reactors or reactor vessels, heaters, exchangers, pipes, pumps, compressors, controllers and columns. Additionally, an equipment item, such as a reactor, dryer, or vessel, can further include one or more zones or sub-zones.

As used herein, the term "overhead line" can mean a line connected at or near a top of a vessel, such as a column.

As used herein, the term "bottom stream" can mean a line connected at or near a bottom of a vessel, such as a column.

As depicted, process flow lines in the FIGURE can be referred to interchangeably as, e.g., lines, pipes, feeds, gases, products, discharges, parts, portions, or streams.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take stripped product from the bottom.

As used herein, the term "a component-rich stream" means that the rich stream coming out of a vessel has a greater concentration of the component than the feed to the vessel.

As used herein, the term "a component-lean stream" means that the lean stream coming out of a vessel has a smaller concentration of the component than the feed to the vessel.

The term "predominant" means a majority, suitably at least 80 wt % and preferably at least 90 wt %.

DETAILED DESCRIPTION

The present invention may be applied to any hydrocarbon stream containing ethylene and ethane, preferably, a dilute proportion of ethylene. A suitable, dilute ethylene stream may typically comprise between about 5 and about 50 wt % ethylene. An FCC dry gas stream is a suitable dilute ethylene stream. Other dilute ethylene streams may also be utilized in the present invention such as coker dry gas streams. Because the present invention is particularly suited to FCC dry gas, the subject application will be described with respect to utilizing ethylene from an FCC dry gas stream.

Now turning to the FIGURE, wherein like numerals designate like components, the FIGURE illustrates a refinery complex 6 that generally includes an FCC unit 10, a product recovery section 90 and a dry gas processing section 140. The FCC unit section 10 includes a reactor 12 and a catalyst regenerator 14. Process variables in the FCC unit 10 typically include a cracking reaction temperature of about 400 C (752° F.) to about 600° C. (1112° F.) and a catalyst regeneration temperature of about 500 C (932° F.) to about 900° C. (1652° F.). Both the cracking and regeneration occur at an absolute pressure below 506 kPa (72.5 psia).

The FIGURE shows a typical FCC reactor 12 in which a heavy hydrocarbon feed or raw oil stream in a distributor 16 is contacted with a regenerated cracking catalyst entering from a regenerated catalyst standpipe 18. Contacting in the FCC reactor 12 may occur in a narrow riser 20, extending upwardly to the bottom of a reactor vessel 22. The contacting of feed and catalyst is fluidized by gas from a fluidizing line 24. In an embodiment, heat from the catalyst vaporizes the hydrocarbon feed or oil, and the hydrocarbon feed is thereafter cracked to lighter molecular weight hydrocarbon products in the presence of the catalyst as both are transferred up the riser 20 into the reactor vessel 22. Inevitable side reactions occur in the riser 20 leaving coke deposits on the catalyst that lower catalyst activity. The cracked light hydrocarbon products are thereafter separated from the coked cracking catalyst using cyclonic separators which may include a primary separator 26 and one or two stages of cyclones 28 in the reactor vessel 22. Gaseous, cracked products exit the reactor vessel 22 through a product outlet 31 to line 32 for transport to a downstream product recovery section 90. The spent or coked catalyst requires regeneration for further use. Coked cracking catalyst, after separation from the gaseous product hydrocarbons, falls into a stripping section 34 where steam is injected through a nozzle to purge any residual hydrocarbon vapor. After the stripping operation, the coked catalyst is carried to the catalyst regenerator 14 through a spent catalyst standpipe 36.

The FIGURE depicts a regenerator 14 known as a combustor, although other types of regenerators are suitable. In the catalyst regenerator 14, a stream of oxygen-containing gas, such as air, is introduced through an air distributor 38 to contact the coked catalyst. Coke is combusted from the coked catalyst to provide regenerated catalyst and flue gas. The catalyst regeneration process adds a substantial amount of heat to the catalyst, providing energy to offset the endothermic cracking reactions occurring in the reactor riser 20. Catalyst and air flow upwardly together along a combustor riser 40 located within the catalyst regenerator 14 and, after regeneration, are initially separated by discharge through a disengager 42. Additional recovery of the regenerated catalyst and flue gas exiting the disengager 42 is achieved using first and second stage separator cyclones 44, 46, respectively within the catalyst regenerator 14. Catalyst separated from flue gas dispenses through dip legs from cyclones 44, 46 while flue gas relatively lighter in catalyst sequentially exits cyclones 44, 46 and exits the regenerator vessel 14 through flue gas outlet 47 in flue gas line 48. Regenerated catalyst is carried back to the riser 20 through the regenerated catalyst standpipe 18. As a result of the coke burning, the flue gas vapors exiting at the top of the catalyst regenerator 14 in line 48 contain CO, $CO_2$, $N_2$ and $H_2O$, along with smaller amounts of other species. Hot flue gas exits the regenerator 14 through the flue gas outlet 47 in a line 48 for further processing.

The FCC product recovery section 90 is in downstream communication with the product outlet 31. In the product recovery section 90, the gaseous FCC product in line 32 is directed to a lower section of an FCC main fractionation column 92. The main fractionation column 92 is also in downstream communication with the product outlet 31. Several fractions of FCC product may be separated and taken from the main fractionation column including a heavy slurry oil from the bottoms in line 93, a light cycle oil in line 95 taken from outlet 95a and a heavy naphtha stream in line 96 taken from outlet 96a. Any or all of lines 93-96 may be cooled and pumped back to the main fractionation column 92 to cool the main fractionation column typically at a higher location. Gasoline and gaseous light hydrocarbons are removed in an overhead line 97 from the main fractionation column 92 and condensed before entering a main column receiver 99. The main column receiver 99 is in downstream communication with the product outlet 31.

An aqueous stream is removed from a boot in the receiver 99. Moreover, a condensed light naphtha stream is removed in condensate line 101 while an overhead stream is removed in overhead line 102 from the receiver 99. The overhead stream in overhead line 102 contains gaseous light hydrocarbons which may comprise a dilute ethylene stream. A portion of the condensed stream in condensate line 101 is refluxed back to the main column in line 103, so the main fractionation column 92 is in upstream communication with the main column receiver 99. A net bottoms stream in a net bottoms line 105 and a net overhead stream in overhead line 102 comprising unstabilized light naphtha may enter a gas recovery section 120 of the product recovery section 90.

The gas recovery section 120 is shown to be an absorption based system, but any gas recovery system may be used, including a cold box system. To obtain sufficient separation of light gas components the gaseous stream in overhead line 102 is compressed in compressor 104. More than one compressor stage may be used, and typically a dual stage compression is utilized to compress the gaseous stream in line 102 to between about 1.2 MPa to about 2.1 MPa (gauge) (180-300 psig) to provide a compressed light vaporous hydrocarbon stream. Three stages of compression may be advantageous to provide additional pressure at least as high as 3.4 MPa (gauge) (500 psig).

The compressed light vaporous hydrocarbon stream in a compressor discharge line 106 may be joined by streams in lines 107 and 108, cooled and delivered to a high pressure receiver 110. An aqueous stream from the receiver 110 may be routed to the main column receiver 99. A gaseous hydrocarbon stream in a high pressure overhead line 112 from the top of the high pressure receiver 110 is routed to a lower end of a primary absorber column 114. In the primary absorber column 114, the gaseous hydrocarbon stream is contacted with the unstabilized light naphtha stream from the net main column receiver bottoms stream in the net main column receiver bottoms line 105 directed to an upper end of the primary absorber column 114 to effect a separation between $C_{3+}$ and $C_{2-}$ hydrocarbons. This separation is further improved by feeding stabilized gasoline from line 135 above the feed inlet for stream 105. The primary absorber column 114 is in downstream communication with an overhead line 102 of the main column receiver via the compressor discharge line 106, the high pressure overhead line 112 and the main column bottoms line 105 of the main column receiver 99. A liquid $C_{3+}$ bottoms stream in an absorber bottoms line 107 is returned to the compressor discharge line 106 prior to cooling. A primary off-gas stream in a primary absorber overhead line 116 from the primary absorber column 114 comprises a dilute ethylene stream which is fed to the lower end of a secondary absorber 118.

The secondary absorber column 118 is in downstream communication with the primary absorber column 114. A circulating stream of light cycle oil in line 121 diverted from line 95 to an upper end of the secondary absorber column 118 absorbs most of the $C_3$-$C_4$ material in the primary off-gas. The secondary absorber column 118 is in downstream communication with the main fractionation column 92. Light cycle oil from the bottom of the secondary absorber column 118 in the secondary absorber bottoms line 119 rich in $C_{3+}$ material is returned to the main fractionation column 92 via the pump-around for line 95. The main fractionation column 92 is in downstream communication with the secondary absorber column 118 via the secondary absorber bottoms line 119. A secondary off-gas stream from the secondary absorber column 118 comprising dry gas of predominantly $C_{2-}$ hydrocarbons with many impurities is removed in the secondary absorber overhead line 122 as a hydrocarbon feed stream to be further processed. Both of the absorber columns 114 and 118 have no condenser or reboiler, but may employ pump-around cooling circuits.

In the high pressure receiver 110, the gaseous hydrocarbon stream exiting in the high pressure overhead line 112 is separated from a high pressure liquid stream comprising $C_{3+}$ hydrocarbons exiting from the bottom of the high pressure receiver 110 in a high pressure bottoms line 124. The high pressure liquid stream in the high pressure bottoms line 124 is sent to a stripper column 126. The stripper column 126 has no condenser but receives the cooled high pressure liquid stream in the high pressure bottoms line 124. Most of the $C_{2-}$ material is removed in the stripper overhead line 108 from the stripper column 126 and is returned to the compressor discharge line 106. A liquid stripper bottoms stream from the stripper column 126 is sent to a debutanizer fractionation column 130 through the stripper bottoms line 128.

The debutanizer fractionation column produces a debutanizer overhead stream in a debutanizer overhead line 132 comprising $C_3$-$C_4$ hydrocarbon product and a debutanized bottoms stream in a debutanized bottoms line 134 comprising stabilized gasoline. A portion of the stabilized gasoline in bottoms line 134 may be recycled in a debutanized recycle line 135 to a top of the primary absorber column above the feed inlet for the main column receiver bottoms line 105 to improve the recovery of $C_{3+}$ hydrocarbons. The debutanizer overhead stream in the debutanizer overhead line 132 comprising $C_3$ and $C_4$ olefins may be used as feed for alkylation or subjected to further processing to recover olefins. In an aspect, the debutanizer overhead line 132 may be fed to an LPG splitter to split $C_3$ hydrocarbons from $C_4$ hydrocarbons. A net debutanized bottom stream in a net debutanized bottoms line 136 may be fractionated in a naphtha splitter column to separate light and heavy naphtha and/or further treated and sent to gasoline storage.

Table 1 shows the range of impurities in the dry gas hydrocarbon feed stream and a typical maximum concentration required for a steam cracking unit.

TABLE 1

| Contaminant | Dry Gas | Feed Requirement |
| --- | --- | --- |
| $H_2S$, vppm | 5000-15000 | 1 |
| Mercaptan, mg/kg | 1-10 | 1 |
| COS, vppm | 5-20 | 1 |
| $CO_2$, vppm | 10000-20000 | 2 |
| CO, vppm | 1000-5000 | 2 |
| $N_2$, wppm | 50000-200000 | 100 |
| NOx, wppm | 10-100 | 5 |
| $O_2$, vppm | 1000-10000 | 2 |
| Acetylene, vppm | 5-20 | 3 |
| $NH_3$, wppm | 1000-10000 | 2 |
| Chlorine, vppm | 20-60 | 37 |
| $AsH_3$, wppb | 50-200 | 20 |

Table 2 shows the range of hydrocarbons and hydrogen that can be present in the dry gas hydrocarbon feed stream. The dry gas stream may have a temperature of about 75° C. (167° F.) to about 125° C. (257° F.) and a pressure of about 1600 kPa (232 psig) to about 1900 kPa (276 psig).

TABLE 2

| Component | mol % |
| --- | --- |
| Hydrogen | 10-30 |
| Methane | 25-40 |
| Ethane | 10-20 |
| Ethylene | 10-20 |
| Propane | 0.25-1.5 |
| Propylene | 1-5 |
| Iso-Butane | 0.1-1.5 |
| n-Butane | 0.01-0.5 |
| 1-Butene | 0.05-0.75 |
| Iso-Butene | 0.05-0.75 |
| Trans-Butene | 0.05-0.75 |
| Cis-Butene | 0.05-0.75 |
| Butadiene | 0 |
| iso-Pentane | 0.05-0.5 |
| n-Pentane | 0-0.05 |
| $C_{6+}$ | 0.05-0.1 |

The hydrocarbon feed stream in the secondary overhead line 122 must be purified in the dry gas processing section 140 to allow for further processing to make steam cracker feed. The dry gas processing section 140 includes a water wash column 50, an absorption unit 60, a selective hydrotreating reactor 80, an adsorption-demethanizer column unit 150, an acid gas adsorption unit 190 and a sweetening adsorption vessel 210.

The hydrocarbon feed stream in the secondary overhead line 122 may be fed to a water wash column 50 to remove both chlorides and ammonia from the hydrocarbon feed stream. Chlorides are removed first to avoid more costly stainless steel equipment downstream. In addition, ammonia removal reduces operating costs for downstream amine treating. A water stream may be introduced to the top of the water wash column in line 52 and counter-currently contacts the hydrocarbon feed stream that enters at the bottom of the water wash column 50. The water wash stream absorbs chlorides and ammonia. A chloride and ammonia-rich aqueous stream in a water wash bottoms line 54 leaves the water wash column 50. Trays in the water wash column 50 enhance vapor-liquid contact. Due to high chloride and carbon dioxide levels, the water wash column 50 and the trays therein may be made of duplex stainless steel. The water wash column may be operated at a temperature of about 40° C. (104° F.) to about 125° C. (257° F.) and a pressure of about 1250 to about 1750 kPa. A washed hydrocarbon feed stream depleted of ammonia and chlorides exit the overhead of the water wash column 50 in a water wash overhead line 56 and enter an absorption unit 60.

In the absorption unit 60, carbon dioxide, hydrogen sulfide and carbonyl sulfide are absorbed from the washed hydrocarbon feed stream by contact with a solvent to provide an absorbed hydrocarbon feed stream which exits the absorption unit 60 in an absorber line 76. In an embodiment, the absorption unit includes two absorber columns 62 and 70. In the first absorber column 62, the hydrocarbon feed stream in the wash bottoms line 56 is fed to the bottom of the first absorber column and counter-currently contacted with a first solvent fed to the top of the first absorber column 62 in a first solvent line 64. The washed hydrocarbon feed stream in the wash overhead line 56 may be passed through the trayed or packed first absorber column 62. The first absorber column 62 may be in downstream communication with the water wash column 50. Acid gases, hydrogen sulfide, carbon dioxide and carbonyl sulfide, are absorbed into the first solvent from line 64. Preferred first solvents include Selexol™ available from UOP LLC in Des Plaines, Ill. and amines such as alkanolamines including diethanol amine (DEA), monoethanol amine (MEA), methyl diethanol amine (MDEA), diisopropanol amine (DIPA), and diglycol amine (DGA). Other amines can be used in place of or in addition to the preferred amines. The resultant first absorbed hydrocarbon feed stream exits an overhead of the first absorber column 62 in a first absorber overhead line 66 with about 5 to about 30 vppm of hydrogen sulfide still remaining in the first absorbed hydrocarbon feed stream. A hydrogen sulfide-rich solvent stream is taken out from a bottom of the first absorber column 62 in a first absorber bottoms line 68. The hydrogen sulfide-rich solvent from the bottom may be regenerated and recycled back to the first absorber column 62 in line 64. The first absorber column 62 may be operated at a temperature of about 40° C. (104° F.) to about 125° C. (257° F.) and a pressure of about 1200 to about 1600 kPa. The temperature of the washed hydrocarbon feed stream in the wash bottoms line 56 may be between about 20° C. (68° F.) and about 80° C. (176° F.) and the temperature of the first solvent stream in solvent line 64 may be between about 20° C. (68° F.) and about 70° C. (158° F.).

Carbon dioxide, hydrogen sulfide and carbonyl sulfide in the hydrocarbon feed stream may still require further removal from the first absorbed hydrocarbon feed stream in the first absorber overhead line 66. In the second absorber column 70, the first absorbed hydrocarbon feed stream in the first absorber overhead line 66 may be fed to the bottom of the second absorber column 70 and counter-currently contacted with a second solvent fed to the top of the second absorber column 70 in a second solvent line 74. The first absorbed hydrocarbon feed stream in the first absorber overhead line 66 may be passed through the trayed or packed second absorber column 70. The second absorber column 70 may be in downstream communication with the water wash column 50 and the first absorber column 62. Acid gases, hydrogen sulfide, carbon dioxide and carbonyl sulfide, are absorbed into the second solvent from line 74. Preferred second solvents include Selexol and alkanolamines as previously mentioned for the first solvent stream in the first solvent line 64. The second absorber column 70 may use an activator in the second solvent that accelerates kinetics and reduces the number of required trays. The activator may comprise piperazine. Other amines can be used in place of or in addition to the preferred amines. The resultant second absorbed hydrocarbon feed stream exits an overhead of the second absorber column 70 in a second absorber overhead line which may be the absorber line 76 with hydrogen sulfide, carbon dioxide and carbonyl sulfide only present in the second absorbed hydrocarbon feed stream at acceptable levels. A carbon dioxide, carbonyl sulfide and hydrogen sulfide-rich solvent stream is taken out from a bottom of the second absorber column 70 in a second absorber bottoms line 78. The carbon dioxide, carbonyl sulfide and hydrogen sulfide-rich solvent from the bottom may be regenerated and recycled back to the second absorber column 70 in line 78. The second absorption column 70 may be operated at a temperature of about 75 C (167° F.) to about 125° C. (257° F.) and a pressure of 1000 to about 1400 [MJA1] kPa. The temperature of the first absorbed hydrocarbon feed stream in the first absorber overhead line 66 may be cooled to between about 20° C. (68° F.) and about 80° C. (176° F.) before entering the second absorber column 70 and the temperature of the second solvent stream in solvent line 74 may be between about 20° C. (68° F.) and about 70° C. (158° F.). An absorbed hydrocarbon feed stream depleted of carbon dioxide, carbonyl sulfide and hydrogen sulfide exit the absorption unit 60 in an absorber line 76. The absorbed hydrocarbon feed stream may comprise no more than about 20 vppm carbon dioxide and about 50 vppm hydrogen sulfide.

An absorbed hydrocarbon feed stream which may comprise the second absorbed hydrocarbon feed stream in the second absorber overhead line 76 may be introduced to a selective hydrotreating reactor 80 to hydrogenate acetylene in the absorbed hydrocarbon feed stream to ethane and ethylene. The selective hydrotreating reactor 80 includes a hydrogenation catalyst in a fixed catalyst bed 82 for conversion of acetylene to ethylene and nitrous oxides and oxygen to water and ammonia. The catalyst bed may use a nickel catalyst such as OleMax 101 catalyst available from Sud-Chemie. Hydrogen present in the hydrocarbon feed stream will be in sufficient quantity to hydrogenate acetylene as well as to lower both $NO_x$ and $O_2$ concentrations. The hydrogenation catalyst utilizes some sulfur, but too much sulfur and carbon dioxide can poison the catalyst. Thus, the selective hydrotreating reactor 80 is located downstream of the water wash column 50 and the absorption unit 60 which remove hydrogen sulfide and carbon dioxide. A hydrogenation sulfiding agent may be added to the hydrocarbon feed stream entering the selective hydrotreating reactor 80 to attenuate catalyst activity to reduce the potential for a temperature runaway particularly as the catalyst ages. Dimethyl disulfide is a suitable hydrogenation sulfiding agent. The selective hydrotreating reactor 80 provides a hydrogenated hydrocarbon feed stream in hydrogenation line 84.

After selective hydrotreating, light gases must be removed from the hydrogenated hydrocarbon feed stream in a pressure swing adsorption-demethanizer column unit 150. Since the pressure swing adsorption-demethanizer column unit 150 runs well below the freezing point of water, water must be removed upstream in a chiller 152 and drier 160. The chiller 152 uses propylene refrigerant to condense most of the water from the hydrogenated hydrocarbon feed stream in the hydrogenation line 84. The condensed water is separated from the hydrogenated hydrocarbon stream in a separator 154 as an aqueous stream in the separator bottoms line 156. The partially dried hydrocarbon stream exits the overhead line 158 of the separator 154 and enters the drier 160. The drier 160 may comprise a bed 162 of hydrophilic adsorbent such as activated alumina, silica gel, a molecular sieve desiccant, activated carbon, zinc X zeolite, calcium Y zeolite, and mixtures thereof which will adsorb water down to a concentration of 1 wppm in a dried hydrocarbon feed stream, at which freezing will not be a problem. The dried hydrocarbon feed stream exits the drier 160 in a drier line 164 and is delivered to the pressure swing adsorption unit 170.

The dried hydrocarbon feed stream includes a heavy materials and light gases. The heavy materials may include hydrocarbons such as ethylene, ethane, propane, propylene and other heavier hydrocarbons. The light gases may include methane and lighter gases.

The pressure swing adsorption unit 170 includes an adsorbent selective for the adsorption of the heavy materials. Examples of an adsorbent selective for the adsorption of the heavy materials include, but are not limited to, a silica gel adsorbent. The adsorbent in the pressure swing adsorption unit 170 does not adsorb the light gases including hydrogen, nitrogen, oxygen, carbon monoxide and methane but selectively adsorbs the heavier materials including heavier gases, carbon dioxide, hydrogen sulfide and ethylene, and heavier hydrocarbons at a higher pressure ranging from about 1000 to about 1200 kPa. The adsorbent in the pressure swing adsorption unit 170 lets the light gases pass in the exhaust line 172. In an exemplary embodiment, at least about 80 wt % of nitrogen and hydrogen present in the hydrocarbon feed stream to the pressure swing adsorption unit 170 is removed from heavier adsorbed gas in the exhaust line 172. Further, at least about 70 wt % of methane present in the hydrocarbon feed stream to the pressure swing adsorption unit 170 is removed from heavier gas in the exhaust line 172 from the pressure swing adsorption unit 170. In another exemplary embodiment, at least about 75 wt % of methane present in the hydrocarbon feed stream to the pressure swing adsorption unit 170 is removed in the pressure swing adsorption unit 170 in the exhaust line 172. The heavy gases adsorbed by adsorbent in the pressure swing adsorption unit 170 are periodically desorbed at a lower pressure ranging from about 20 to about 210 kPa and further processed in the heavy line 174.

The heavy hydrocarbon feed stream in the heavy line 174 may further include a remaining portion of light gases adsorbed and desorbed by the pressure swing adsorption unit 170 with the heavy materials. The adsorption zone effluent stream in the heavy line 174 may have a pressure in the range of about 20 to about 210 kPa (gauge). The heavy hydrocarbon feed stream in the heavy line 174 may be compressed in a compressor 176 to provide a compressed heavier hydrocarbon feed stream in the heavy line 174. In accordance with an embodiment, the compressor 176 may be a two-stage compressor. In one example, the compressed heavy hydrocarbon feed stream in the heavy line 174 may have a pressure of at least about 2 to about 6 MPa (gauge). The compressed heavy hydrocarbon feed stream in the heavy line 174 is passed to a cooler 178 for cooling the heavy hydrocarbon feed stream. In an exemplary embodiment, the compressed heavy hydrocarbon feed stream is cooled to a temperature of no lower than about $-30°$ C. ($-22°$ F.) in the cooler 178. In another exemplary embodiment, the compressed heavy hydrocarbon feed stream is cooled to a temperature of no lower than about $-20°$ C. ($-4°$ F.) in the cooler 178.

A cooled heavy hydrocarbon feed stream is withdrawn from the cooler 178 and passed to a demethanizer column 180. In the demethanizer column 180, the $C_{2-}$ hydrocarbon product is fractionated, such as by conventional distillation, to provide a demethanizer overhead stream in a demethanizer overhead line 182 and a demethanized bottoms stream in a demethanizer bottoms line 184. The demethanizer overhead stream is the net vapor stream taken off the overhead of a demethanizer overhead receiver. The demethanizer overhead stream in the demethanizer overhead line 182 includes ethylene, ethane and a remaining amount of methane, hydrogen and nitrogen that was adsorbed and desorbed by the pressure swing adsorption unit 170. The demethanizer overhead stream in the demethanizer overhead line 182 may be recycled to the pressure swing adsorption unit 170 to recover ethylene that may be retained in the demethanizer overhead stream. In various embodiments, the demethanizer overhead stream 182 may pass through the cooler 178 to indirectly heat exchange with the compressed heavy hydrocarbon feed stream in heavy line 174 to cool the heavy hydrocarbon feed stream and heat the demethanizer overhead stream 182 prior to being recycled to the inlet of the pressure swing adsorption unit 170. The demethanizer column 180 operates at significantly warmer temperatures of between about $-30°$ C. ($-22°$ F.) and about $-50°$ C. ($-58°$ F.) at suitably least about $-45°$ C. ($-49°$ F.) and preferably at least about $-40°$ C. ($-40°$ F.) rather than at a cryogenic demethanizer column temperature of around $-95°$ C. ($-140°$ F.). Thus, the overall ethylene separation can be met without using an ethylene refrigerant system. This permits the demethanizer column 180 to be cooled with a propylene refrigerant which can cool down to temperatures below $-49°$ C. ($-56°$ F.) rather than an ethylene refrigerant-based cooling system which is necessary to cool down to temperatures below $-100°$ C. ($-148°$ F.) for recovering ethylene.

A net demethanizer bottoms stream is withdrawn from the bottom of the demethanizer column 180 in a net demethanized bottoms line 184. The net demethanized bottoms stream includes ethylene, ethane and the heavier hydrocarbons. In an embodiment, the net demethanized bottoms stream includes less than about 1 wt % of the light gases lighter than ethylene present in the hydrocarbon feed stream fed to the pressure swing adsorption unit 170 in the drier line 164. The net demethanized bottoms stream in the net demethanizer bottoms line 184 predominantly includes ethylene and ethane. In accordance with an exemplary embodiment, the net demethanizer bottoms stream includes at least about 85 wt % and preferably at least about 90 wt % of the ethylene present in the hydrocarbon feed stream fed to the pressure swing adsorption unit 170 in the drier line 164.

The demethanized bottoms stream may be at a pressure of between about 2 and about 6 MPa (gauge) and will still have concentrations of hydrogen sulfide, carbonyl sulfide, carbon dioxide, mercaptans and arsine that exceed specifications for a stream cracking unit. The demethanized bottoms stream may be delivered to an acid gas adsorption unit 190 for adsorbing hydrogen sulfide, carbonyl sulfide and carbon dioxide from the net demethanized bottoms stream. The acid gas adsorption unit may include an adsorption vessel 192 including an adsorbent bed 194 with acid gas adsorbents that adsorb hydrogen sulfide, carbonyl sulfide and carbon dioxide by contact with the net demethanized bottom stream to provide an acid gas adsorbed net bottoms stream in an acid gas adsorbed line 196. In an aspect, the acid gas adsorption unit 190 may include a first adsorption vessel 192 with a first adsorbent bed 194 and a second adsorption vessel 198 with a second adsorbent bed 200 each with acid gas adsorbents that adsorb hydrogen sulfide, carbonyl sulfide and carbon dioxide by contact with the net demethanized bottom stream to provide an acid gas adsorbed net bottoms stream in the acid gas adsorbed line 196. In one aspect, the first adsorption vessel 192 and the second adsorption vessel 198 may operate in swing bed mode. In an embodiment, valving is arranged such that the first adsorbent bed 194 in the first adsorption vessel 192 receives the demethanized bottoms stream in the net demethanized bottoms line 184 to adsorb acid gases while the second adsorbent bed 200 in the second adsorption vessel 198 is out of communication with the demethanized bottoms line 184. The second adsorbent bed 200 may undergo regeneration with a desorption gas such as nitrogen gas from regeneration line 202 to remove adsorbed acid gases from the second adsorbent bed 194 while out of communication with the demethanized bottoms line 184. When the first adsorbent bed 194 is spent, valving may be rearranged such that the second adsorbent bed 200 in the second adsorption vessel 198 receives the demethanized bottoms stream in net demethanized bottoms line 184 to adsorb acid gases while the first adsorbent bed 194 in the first adsorption vessel 192 is out of communication with the demethanized bottoms line 184. The first adsorbent bed 194 may undergo regeneration with the desorption gas from the regeneration line 202 to remove adsorbed acid gases from the first adsorbent bed 194 while out of communication with the demethanized bottoms line 184.

The acid gas adsorbent in the beds 194 and 200 may be CG-731 adsorbent available from UOP LLC in Des Plaines, Ill. The concentration of acid gases, hydrogen sulfide, carbonyl sulfide and carbon dioxide, in the acid gas adsorbed line 196 may be no more than about 1 vppm each.

The acid gas adsorbed demethanized bottoms stream in acid gas adsorbed line 196 still may contain arsine and mercaptans concentrations over specified levels for a steam cracking unit. Hence, the acid gas adsorbed demethanized bottoms stream in acid gas adsorbed line 196 may be fed to a sweetening adsorption vessel 210 containing a sweet adsorbent bed 212. The acid gas adsorbed demethanized bottoms stream is contacted with the a sweetening adsorbent in the sweet adsorbent bed 212 to adsorb mercaptans and arsines and provide a sweetened demethanized net bottoms stream in sweet line 214. The sweetening adsorbent may be GB-238 adsorbent available from UOP LLC in Des Plaines, Ill. The sweetened demethanized net bottoms stream in the sweet line 214 may comprise no more than about 1 vppm of mercaptans and no more than about 0.02 vppm of arsine. The sweetened demethanized bottom stream in sweet line 214 may have a pressure of about 1.5 to about 2 MPa.

The sweetened demethanized bottoms stream in sweet line 214 may be delivered to a steam cracking unit 220. The steam cracking unit 220 may include a fractionation section that separates ethane and lighter hydrocarbons from heavier hydrocarbons in a deethanizer column and an ethylene splitter column to recover ethylene from ethane. The ethane and heavier hydrocarbons comprising at least a portion of the sweetened demethanized bottoms stream may be forwarded to a steam cracking furnace that cracks ethane and heavier hydrocarbons to produce ethylene product.

In an aspect, ethylene may be recovered from the sweetened demethanized stream in the sweet line 214 before an ethylene depleted demethanized bottoms stream is delivered to the stream cracking unit 220. A $C_2$ splitter column 230 may be in downstream communication with the demethanizer column 180 and the sweet adsorbent vessel 210 and be configured to recover ethylene from the sweetened demethanized bottoms stream in sweet line 214. In an exemplary embodiment, a deethanizer column (not shown) may also be utilized between the demethanizer column 180 and the $C_2$ splitter column 230 to separate a deethanizer overhead stream comprising predominantly ethane and ethylene from a deethanized $C_{3+}$ bottoms stream which may be recovered and subsequently sending the deethanizer overhead stream to the $C_2$ splitter column 210. However, it may not be necessary to first separate heavier hydrocarbons from the $C_2$ hydrocarbons in a deethanizer column because in the $C_2$ splitter column 230 the heavier hydrocarbons should go with the ethane bottoms stream. The $C_2$ splitter column 230 may recover a high purity ethylene product stream such as greater than 99.5 mol % in a net splitter overhead line 232 and an ethane rich bottoms stream in a splitter bottoms line 234. The ethane-rich stream in the splitter bottoms line 234 may be delivered to the steam cracking unit 220 as steam cracking feed. The $C_2$ splitter column 230 may operate at about 3.5 to about 4 MPa and an overhead temperature of about −30° C. (−22° F.) to about −50° C. (−58° F.).

Accordingly, a waste dry gas stream can be utilized to produce a high purity ethylene stream and a steam cracker product stream.

Specific Embodiments

While the following is described in conjunction with specific embodiments, it will be understood that this description is intended to illustrate and not limit the scope of the preceding description and the appended claims.

A first embodiment of the invention is a process for removing light gases from a hydrocarbon feed stream including ethylene, ethane and heavier hydrocarbons, the process comprising (a) absorbing carbon dioxide, hydrogen sulfide and carbonyl sulfide from the hydrocarbon feed stream by contact with a solvent to provide an absorbed hydrocarbon feed stream; (b) hydrogenating acetylene in the absorbed hydrocarbon feed stream to ethane and ethylene to provide a hydrogenated hydrocarbon feed stream; (c) removing a heavier hydrocarbon feed stream from light gases comprising hydrogen, carbon monoxide, nitrogen and methane in the hydrogenated hydrocarbon feed stream; and (d) demethanizing the heavier hydrocarbon feed stream to provide an overhead stream comprising hydrogen, carbon monoxide, nitrogen and methane and a net bottoms stream comprising ethylene, ethane and the heavier hydrocarbons. An embodiment of the invention is one, any or all of prior embodiments in this paragraph up through the first embodiment in this paragraph further comprising drying the hydrogenated hydrocarbon feed stream before the selective adsorption step by contacting the hydrogenated hydrocarbon feed stream with a hydrophilic adsorbent. An embodiment of the invention is one, any or all of prior embodiments in this paragraph up through the first embodiment in this paragraph further comprising chilling and condensing water from the hydrogenated hydrocarbon feed stream before contact with the hydrophilic adsorbent. An embodiment of the invention is one, any or all of prior embodiments in this paragraph up through the first embodiment in this paragraph further comprising washing the hydrocarbon feed stream with water to absorb chlorides and ammonia from the hydrocarbon feed stream before the absorption step. An embodiment of the invention is one, any or all of prior embodiments in this paragraph up through the first embodiment in this paragraph further comprising recycling the demethanizing overhead stream to the removal step. An embodiment of the invention is one, any or all of prior embodiments in this paragraph up through the first embodiment in this paragraph wherein the absorption step comprises absorbing carbon dioxide, hydrogen sulfide and carbonyl sulfide from the hydrocarbon feed stream by contact with a first solvent to remove carbon dioxide and most of the hydrogen sulfide and then by contact with a second solvent to remove carbon dioxide, carbonyl sulfide and hydrogen sulfide to low levels and provide the absorbed hydrocarbon feed stream. An embodiment of the invention is one, any or all of prior embodiments in this paragraph up through the first embodiment in this paragraph further comprising acid gas adsorbing hydrogen sulfide, carbonyl sulfide and carbon dioxide from the net bottoms stream by contacting the net bottoms stream with an acid gas adsorbent to provide an acid gas adsorbed net bottoms stream. An embodiment of the invention is one, any or all of prior embodiments in this paragraph up through the first embodiment in this paragraph further comprising regenerating a second acid gas adsorbent bed with a desorption gas while acid gas adsorbing hydrogen sulfide, carbonyl sulfide and carbon dioxide from the net bottoms stream by contacting the net bottoms stream with a first acid gas adsorbent bed to provide the acid gas adsorbed net bottoms stream. An embodiment of the invention is one, any or all of prior embodiments in this paragraph up through the first embodiment in this paragraph further comprising sweet adsorbing mercaptans and arsine from the acid gas adsorbed net bottoms stream by contacting the net bottoms stream with a sweetening adsorbent to provide a sweetened net bottoms stream. An embodiment of the invention is one, any or all of prior embodiments in this paragraph up through the first embodiment in this paragraph further comprising delivering the net bottoms stream to a steam cracking unit to produce olefins. An embodiment of the invention is one, any or all of prior embodiments in this paragraph up through the first embodiment in this paragraph further adding a hydrogenation sulfiding agent to attenuate catalyst activity and to reduce the potential for a temperature runaway. An embodiment of the invention is one, any or all of prior embodiments in this paragraph up through the first embodiment in this paragraph, wherein the demethanizer column operates at a bottoms temperature of between about −30 and about −50° C. An embodiment of the invention is one, any or all of prior embodiments in this paragraph up through the first embodiment in this paragraph, wherein the heavier hydrocarbon feed stream is compressed prior to being passed to the demethanizer column.

A second embodiment of the invention is a process for removing light gases from a hydrocarbon feed stream to a steam cracker unit including ethane and heavier hydrocarbons, the process comprising (a) absorbing carbon dioxide, hydrogen sulfide and carbonyl sulfide from the hydrocarbon feed stream by contact with a solvent to provide an absorbed hydrocarbon feed stream; (b) hydrogenating acetylene in the absorbed hydrocarbon feed stream to ethane and ethylene to provide a hydrogenated hydrocarbon feed stream; (c) selectively removing a heavier hydrocarbon feed stream from light gases comprising hydrogen, nitrogen, carbon monoxide and methane from the hydrogenated hydrocarbon feed stream in an adsorption zone to provide the heavier hydrocarbon feed stream; (d) demethanizing the heavier hydrocarbon feed stream to provide an overhead stream comprising hydrogen, nitrogen, carbon monoxide and methane and a net bottoms stream comprising ethylene, ethane and the heavier hydrocarbons; and (e) steam cracking at least a portion of the net bottoms stream to produce olefins. An embodiment of the invention is one, any or all of prior embodiments in this paragraph up through the second embodiment in this paragraph further comprising drying the hydrogenated hydrocarbon feed stream before the selective adsorption step by chilling and condensing water from the hydrogenated hydrocarbon feed stream and contacting the hydrogenated hydrocarbon feed stream with a hydrophilic adsorbent. An embodiment of the invention is one, any or all of prior embodiments in this paragraph up through the second embodiment in this paragraph further comprising washing the hydrocarbon feed stream with water to absorb chlorides and ammonia from the hydrocarbon feed stream before the absorption step. An embodiment of the invention is one, any or all of prior embodiments in this paragraph up through the second embodiment in this paragraph wherein the absorption step comprises absorbing carbon dioxide, hydrogen sulfide and carbonyl sulfide from the hydrocarbon feed stream by contact with a first solvent to remove carbon dioxide and most of the hydrogen sulfide and then by contact with a second solvent to remove carbon dioxide, carbonyl sulfide and hydrogen sulfide to low levels and provide the absorbed hydrocarbon feed stream. An embodiment of the invention is one, any or all of prior embodiments in this paragraph up through the second embodiment in this paragraph further comprising acid gas adsorbing hydrogen sulfide, carbonyl sulfide and carbon dioxide from the net bottoms stream by contacting the net bottoms stream with an acid gas adsorbent to provide an acid gas adsorbed net bottoms stream; and sweetening adsorbing mercaptans and arsine from the acid gas adsorbed net bottoms stream by contacting the net bottoms stream with a sweetening adsorbent to provide a sweetened net bottoms stream.

A third embodiment of the invention is a process for removing light gases from a hydrocarbon feed stream including ethylene, ethane and heavier hydrocarbons, the process comprising (a) washing the hydrocarbon feed stream with water to absorb chlorides and ammonia from the hydrocarbon feed stream to provide a washed hydrocarbon feed stream; (b) absorbing carbon dioxide, hydrogen sulfide and carbonyl sulfide from the washed hydrocarbon feed stream by contact with a solvent to provide an absorbed hydrocarbon feed stream; (c) hydrogenating acetylene in the absorbed hydrocarbon feed stream to ethane and ethylene to provide a hydrogenated hydrocarbon feed stream; (d) drying the hydrogenated hydrocarbon feed stream by contacting the hydrogenated hydrocarbon feed stream with a hydrophilic adsorbent to provide a dried hydrocarbon feed stream; (e) selectively removing a heavier hydrocarbon feed stream from light gases comprising hydrogen, nitrogen, carbon monoxide, and methane from the dried hydrogenated hydrocarbon feed stream in an adsorption zone to provide a heavier hydrocarbon feed stream; and (f) demethanizing the heavier hydrocarbon feed stream to provide an overhead stream comprising hydrogen, nitrogen, carbon monoxide, and methane and a net bottoms stream comprising ethylene, ethane and the heavier hydrocarbons. An embodiment of the invention is one, any or all of prior embodiments in this paragraph up through the third embodiment in this paragraph further comprising chilling and condensing water from the hydrogenated hydrocarbon feed stream before contacting the hydrogenated hydrocarbon feed stream with a hydrophilic adsorbent.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for removing light gases from a hydrocarbon feed stream including ethylene, ethane and heavier hydrocarbons, the process comprising:
   (a) absorbing carbon dioxide, hydrogen sulfide and carbonyl sulfide from the hydrocarbon feed stream by contact with a solvent to provide an absorbed hydrocarbon feed stream;
   (b) hydrogenating acetylene in the absorbed hydrocarbon feed stream to ethane and ethylene to provide a hydrogenated hydrocarbon feed stream;
   (c) removing a heavier hydrocarbon feed stream from light gases comprising hydrogen, carbon monoxide, nitrogen and methane in the hydrogenated hydrocarbon feed stream; and
   (d) demethanizing the heavier hydrocarbon feed stream to provide an overhead stream comprising hydrogen, carbon monoxide, nitrogen and methane and a net bottoms stream comprising ethylene, ethane and the heavier hydrocarbons.

2. The process of claim 1 further comprising drying the hydrogenated hydrocarbon feed stream before the selective adsorption step by contacting the hydrogenated hydrocarbon feed stream with a hydrophilic adsorbent.

3. The process of claim 2 further comprising chilling and condensing water from the hydrogenated hydrocarbon feed stream before contact with the hydrophilic adsorbent.

4. The process of claim 1 further comprising washing the hydrocarbon feed stream with water to absorb chlorides and ammonia from the hydrocarbon feed stream before the absorption step.

5. The process of claim 1 further comprising recycling the demethanizing overhead stream to the removal step.

6. The process of claim 1 wherein the absorption step comprises absorbing carbon dioxide, hydrogen sulfide and carbonyl sulfide from the hydrocarbon feed stream by contact with a first solvent to remove carbon dioxide and most of the hydrogen sulfide and then by contact with a second solvent to remove carbon dioxide, carbonyl sulfide and hydrogen sulfide to low levels and provide said absorbed hydrocarbon feed stream.

7. The process of claim 1 further comprising acid gas adsorbing hydrogen sulfide, carbonyl sulfide and carbon dioxide from said net bottoms stream by contacting said net bottoms stream with an acid gas adsorbent to provide an acid gas adsorbed net bottoms stream.

8. The process of claim 7 further comprising regenerating a second acid gas adsorbent bed with a desorption gas while acid gas adsorbing hydrogen sulfide, carbonyl sulfide and carbon dioxide from said net bottoms stream by contacting said net bottoms stream with a first acid gas adsorbent bed to provide said acid gas adsorbed net bottoms stream.

9. The process of claim 7 further comprising sweet adsorbing mercaptans and arsine from said acid gas adsorbed net bottoms stream by contacting said net bottoms stream with a sweetening adsorbent to provide a sweetened net bottoms stream.

10. The process of claim 1 further comprising delivering said net bottoms stream to a steam cracking unit to produce olefins.

11. The process of claim 1 further adding a hydrogenation sulfiding agent to attenuate catalyst activity and to reduce the potential for a temperature runaway.

12. The process of claim 1, wherein the demethanizer column operates at a bottoms temperature of between about −30 and about −50° C.

13. The process of claim 1, wherein the heavier hydrocarbon feed stream is compressed prior to being passed to the demethanizer column.

14. A process for removing light gases from a hydrocarbon feed stream to a steam cracker unit including ethane and heavier hydrocarbons, the process comprising:
   (a) absorbing carbon dioxide, hydrogen sulfide and carbonyl sulfide from the hydrocarbon feed stream by contact with a solvent to provide an absorbed hydrocarbon feed stream;
   (b) hydrogenating acetylene in the absorbed hydrocarbon feed stream to ethane and ethylene to provide a hydrogenated hydrocarbon feed stream;
   (c) selectively removing a heavier hydrocarbon feed stream from light gases comprising hydrogen, nitrogen, carbon monoxide and methane from the hydrogenated hydrocarbon feed stream in an adsorption zone to provide said heavier hydrocarbon feed stream;
   (d) demethanizing the heavier hydrocarbon feed stream to provide an overhead stream comprising hydrogen, nitrogen, carbon monoxide and methane and a net bottoms stream comprising ethylene, ethane and the heavier hydrocarbons; and
   (e) steam cracking at least a portion of said net bottoms stream to produce olefins.

15. The process of claim 14 further comprising drying the hydrogenated hydrocarbon feed stream before the selective adsorption step by chilling and condensing water from the hydrogenated hydrocarbon feed stream and contacting the hydrogenated hydrocarbon feed stream with a hydrophilic adsorbent.

16. The process of claim 14 further comprising washing the hydrocarbon feed stream with water to absorb chlorides and ammonia from the hydrocarbon feed stream before the absorption step.

17. The process of claim 14 wherein the absorption step comprises absorbing carbon dioxide, hydrogen sulfide and carbonyl sulfide from the hydrocarbon feed stream by contact with a first solvent to remove carbon dioxide and most of the hydrogen sulfide and then by contact with a second solvent to remove carbon dioxide, carbonyl sulfide and hydrogen sulfide to low levels and provide said absorbed hydrocarbon feed stream.

18. The process of claim 14 further comprising acid gas adsorbing hydrogen sulfide, carbonyl sulfide and carbon dioxide from said net bottoms stream by contacting said net bottoms stream with an acid gas adsorbent to provide an acid gas adsorbed net bottoms stream; and sweetening adsorbing mercaptans and arsine from said acid gas adsorbed net bottoms stream by contacting said net bottoms stream with a sweetening adsorbent to provide a sweetened net bottoms stream.

19. A process for removing light gases from a hydrocarbon feed stream including ethylene, ethane and heavier hydrocarbons, the process comprising:
   (a) washing the hydrocarbon feed stream with water to absorb chlorides and ammonia from the hydrocarbon feed stream to provide a washed hydrocarbon feed stream;
   (b) absorbing carbon dioxide, hydrogen sulfide and carbonyl sulfide from the washed hydrocarbon feed stream by contact with a solvent to provide an absorbed hydrocarbon feed stream;

(c) hydrogenating acetylene in the absorbed hydrocarbon feed stream to ethane and ethylene to provide a hydrogenated hydrocarbon feed stream;

(d) drying the hydrogenated hydrocarbon feed stream by contacting the hydrogenated hydrocarbon feed stream with a hydrophilic adsorbent to provide a dried hydrocarbon feed stream;

(e) selectively removing a heavier hydrocarbon feed stream from light gases comprising hydrogen, nitrogen, carbon monoxide, and methane from the dried hydrogenated hydrocarbon feed stream in an adsorption zone to provide a heavier hydrocarbon feed stream; and (f) demethanizing the heavier hydrocarbon feed stream to provide an overhead stream comprising hydrogen, nitrogen, carbon monoxide, and methane and a net bottoms stream comprising ethylene, ethane and the heavier hydrocarbons.

20. The process of claim 19 further comprising chilling and condensing water from the hydrogenated hydrocarbon feed stream before contacting the hydrogenated hydrocarbon feed stream with a hydrophilic adsorbent.

* * * * *